(12) United States Patent
Toniatti et al.

(10) Patent No.: US 6,753,419 B1
(45) Date of Patent: Jun. 22, 2004

(54) DNA MOLECULES ENCODING HORMONE-DEPENDENT FORMS OF THE ADENO-ASSOCIATED VIRUS REP PROTEINS

(75) Inventors: Carlo Toniatti, Rome (IT); Cira Rinaudo, Palermo (IT); Gennaro Ciliberto, Rome (IT)

(73) Assignee: Instituto di Ricerche di Biologia Molecolare P. Angeletti S.p.A., Pomezia (IT)

( * ) Notice: Subject to any disclaimer, the term of this patent is extended or adjusted under 35 U.S.C. 154(b) by 0 days.

(21) Appl. No.: 09/554,958

(22) PCT Filed: Nov. 20, 1998

(86) PCT No.: PCT/IT98/00329

§ 371 (c)(1),
(2), (4) Date: Jul. 7, 2000

(87) PCT Pub. No.: WO99/27110

PCT Pub. Date: Jun. 3, 1999

(30) Foreign Application Priority Data

Nov. 21, 1997 (IT) ........................................ RM97A0724

(51) Int. Cl.[7] .............................................. C07H 21/04
(52) U.S. Cl. .................. 536/23.4; 424/93.2; 424/185.1; 424/192.1; 424/198.1; 424/199.1; 435/69.1; 435/69.7; 435/320.1; 435/455; 435/457; 435/458; 530/350; 536/23.1; 536/23.5; 536/23.51; 536/23.72
(58) Field of Search ........................... 424/93.2, 199.1, 424/192.1, 185.1, 198.1; 435/69.1, 69.7, 320.1, 455, 457, 458; 530/350; 536/23.1, 23.5, 23.72, 23.4, 23.51

(56) References Cited

FOREIGN PATENT DOCUMENTS

| WO | 95 13392 | 5/1995 |
|----|----------|--------|
| WO | 96 12010 | 4/1996 |
| WO | 96 17947 | 6/1996 |
| WO | 96 36364 | 11/1996 |

OTHER PUBLICATIONS

Mattoni et al., "Regulation of Protein Activities by Fusion to Steroid Binding Domains," Methods in Cell Biology, vol. 43, 1994, pp. 335–352.

Yang et al., "Mutational analysis of the adeno–associated virus rep gene," Journal of Virology, vol. 66, No. 10, Oct. 1992, pp. 6058–6069.

Vegeto et al., "The mechanism of RU486 antagonism is dependent on the conformation of the carboxyl–terminal tail of the human progesterone receptor," CELL, No. 69, 1992, pp. 703–713.

Holscher et al., "Cell lines inducibly expressing the adeno=associated virus (AAV) rep gene: requirements for productive replication of rep–negative AAV mutants," Journal of Virology, vol 68., No. 11, Nov. 1994, pp. 7169–7177.

*Primary Examiner*—Ulrike Winkler
(74) *Attorney, Agent, or Firm*—Anna L. Cocuzzo; Jack L. Tribble

(57) ABSTRACT

The subject matters of this invention are the hormone-dependent forms of Rep 78 and Rep 68 proteins of the Adeno-associated virus (AAV), obtained by the fusion of their specific mutants with the hormone binding domain (HBD) of steroid hormone receptors, and the DNA sequences coding for them. The invention also refers to a method for the hormonal regulation of the activity of the fusion products Rep78/68-HBD, inserted into eucaryotic cells utilizing viral or non-viral systems, in order to direct the stable integration of DNA sequences in specific regions of the host human genome for therapeutic purposes. The fusion products Rep78/68-HBD are also utilized to generate viral hybrid vectors (i.e. adenovirus vectors AAV) and for generating recombinant vectors AAV.

15 Claims, 12 Drawing Sheets

Fusion Proteins Rep/PR

Rescue-replication experiments with fusion proteins Rep/PR (in cells 293)

C-terminal deletion of Rep68/78

RepΔC-520 — PKRVRESVAQPSTSSD 520
N1 + N2 + N3

RepΔC-504 — KKRPAPSDADISE 504
N1 + N2

RepΔC-491 — YVKKGGA 491
N1

RepΔC-484 — 484

FIGURE 3

RepΔ/PR muteines

Junction sequence with NLS

RepΔN-P

1 ──[ Rep | PR-HBD ]── 
  1   484  635        891

VEHEFGGRKFKKFNKVR

Rep1ΔN/P

1 ──[ Rep | PR-HBD ]──
  1   491  639        891

VEHEFYVKKGGALEFKKFNKVR
N1

Rep1ΔN/P

1 ──[ Rep | PR-HBD ]──
  1   491  642        891

VEHEFYVKKGGALEFNKVR
N1

FIGURE 8

DNA MOLECULES ENCODING HORMONE-DEPENDENT FORMS OF THE ADENO-ASSOCIATED VIRUS REP PROTEINS

CROSS REFERENCE TO RELATED APPLICATION

The present application is the national stage under 35 U.S.C. 371 of PCT/IT98/00329, filed Nov. 20, 1998, which claims priority under § 119(a) to Italian application serial no. RM97A000724, filed Nov. 21, 1997.

DESCRIPTION

1. Field of the Invention

The present invention refers to the field of molecular biology and particularly to the possibility of finely controlling important gene functions for the somatic gene therapy. More specifically, the present invention provides a system for generating forms of some Rep proteins of Adeno-associated virus (AAV) dependant on steroid hormones. The invention also refers to the regulation of the AAV Rep proteins activity to direct the integration of recombinant DNA sequences within specific regions of human host-cell genomic DNA.

2. State of the Art

The integration of therapeutic genes into specific DNA sites of actively dividing cells and of non dividing cells, accompanied by prolonged expression, is the optimal strategy for somatic gene therapy.

The Adeno-associated virus (AAV) has the unique capacity of preferentially integrating its viral DNA into defined regions of the cellular genome, thus reducing the risk of insertional mutagenesis associated with other viruses, e.g. retroviruses that integrate in totally random positions.

The Adeno-associated virus (AAV) is a non-pathogenic small virus, with a single-stranded DNA, not capsized, belonging to the parvovirus family (Balagué et al, 1997). AAV requires coinfection with a helper virus (adenovirus or herpes virus) or the host cells exposition to genotoxic agents (e.g. heat shock, hydroxyurea, UV light and X-rays) in order to undertake a productive infection. In the absence of a helper virus the AAV genome integrates into the chromosomal DNA to generate a latent infection. Analysis of flanking sequences of the provirus integrated genome, as the FISH analysis (in situ hybridisation with fluorescent probes) from latent infected cells, has revealed that the integration of the AAV genome is preferentially targeted to a specific site (called aavsl) localised in the q- terminus of the chromosome 19 (19q13-qter) (Kotin, R M, et al, 1990, PNAS USA, 87:2211–2215; Samulski. R J et al, 1991, EMBO J. 10:3941–3950]). The specificity of the integration refers to a spectrum of 60%–94% of the cases, depending on the cellular lines utilised and on the experimental conditions. This feature reduces the probability of insertional mutagenesis deriving from the random integration of the viral genome. Moreover, the absence of powerful transcription regulatory elements in the AAV genome makes it unlikely that the AAV integration in the aavsl site may be responsible of the transcription activation of endogenous chromosomal genes.

The integrated genome AAV can be rescued and replicated, if the cells containing an integrated provirus are superinfected with a helper virus like the Ad.

The AAV genome is a linear single-stranded DNA 4680 bp long, containing two sequences coding for proteins (ORFs=Open Reading Frames), three promoters (p5, p19 and p40), and an ITR sequence (Inverted Terminal Repeat sequence) of 145 bp, located at each end of the genome. The two ORFs code for non structural (Rep) and structural (Cap) proteins respectively (Kotin, R M, et al, 1990, PNAS USA, 87:2211–2215; Samulski. R J et al, 1991, EMBO J. 10:3941–3950).

The AAV ORF rep codes for four overlapping proteins. More specifically, the rep-coding ORF has two promoters located at map positions 5 (promoter 5, p5) and 19 (promoter 19, p19). The transcripts originated by each one of those two promoters share a common intron near to the 3' terminus of the reading frame and to the polyadenilation site. The intron is utilised only in a subpopulation of the RNA messenger produced. Therefore, the ORF for rep generates four different mRNAs and the corresponding proteins: Rep78 and Rep68, expressed under control of p5 and Rep52 and Rep40, expressed under control of p19. Rep68 and Rep40 are coded by RNA transcripts that undergo a maturation process called "splicing" leading to the intron excision. Mutational analysis has shown the functional activities of the various Rep proteins.

Rep78 and Rep68 are multifunctional proteins that play a crucial role in the AAV replication. Rep78 is 621 amino acids long while Rep68 is 536 amino acids long: Rep78 and Rep68 differ only in their carboxy-terminal end, while the first 529 amino acids are identical in the two peptides. Rep78 and Rep68 share similar biochemical properties: both perform activities that are required for the AAV DNA replication, including the capacity of binding the RBS (Rep Binding Site) in the ITRs, and of cleaving site-specifically in a single strand manner the trs (terminal resolution site) present in the ITRs. Furthermore, Rep78 and Rep68 act as DNA-DNA and DNA-RNA helicases, have an ATP-ase activity and are capable of regulating positively or negatively both AAV promoters and heterologous promoters. Up to today evident functional differences between Rep78 and Rep68 have not been observed. Rep52 and Rep40, which do not show binding activity or endonucleasic DNA activity, are nevertheless important for the AAV infective cycle, as they promote the accumulation of single-stranded capsized genome of AAV.

AAV integration mechanisms during the non productive infection were not entirely clarified. Anyhow, it was clearly established that, beside undetermined cellular factors, two viral elements are required: the ITRs and the Rep78/68 (Carter, B J. in "Handbook of Parvoviruses", ed. P. Tijsser, CRC Press, pp. 155–168, Samulski, R W096/36364). This conclusion is the direct consequence of many observations: firstly, recombining AAV vectors lacking of the rep and cap coding sequences do not specifically integrate into chromosome 19. Secondly, a RBS and a potential flanking trs were identified into the preferential genomic integration site aavsl, and it was proved that Rep68/78 can simultaneously bind the RBS present in ITRs and in aavsl, thus bridging the two DNA sequences. Moreover, utilising an ex vivo assay it was proved that a 33 bp sequence comprising the RBS and the trs in aavsl is the shortest sequence required in order to obtain the targeted integration of AAV into a DNA propagated as episome. Even more interesting is the observation that the two elements required for the AAV site-specific integration, function with a rather high efficiency even when utilised outside of the viral genome context. Actually, it was proved that plasmids bearing a rep expressing cassette can promote, when transfected in cells, the site-specific integration of a transgene flanked by ITR (integration cassette) contained either in the same or in a cotransfected plasmid.

Those experiments overall prove that it is possible to utilise the AAV integration mechanism in a different context from that of the AAV genome. This is of great relevance in the field of somatic gene therapy, because the primary limitation of AAV use for the somatic gene therapy is the low packaging limit of the AAV virion, that cannot exceed 4.5 Kb. As a recombining vector AAV able to integrate specifically in the human chromosome 19 ought to contain Rep78 and/or 68 cDNA (about 2000 nt) as well, the wider DNA sequence (e.g. transcription regulating regions 5' and 3'+transgene) transductable with the AAV vector could not be longer than 2–2.5 Kb.

These dimensional limitations could be overcome either by transducing the ITR-flanked transgene and the rep expression cassette with a non-viral system, or by the introduction of those elements into a viral vector with a wider cloning capacity (e.g. adenovirus, baculovirus, herpes virus, etc.) (as disclosed in the Italian patent application RM97A000200, priority date Apr. 8, 1997). Whatever the selected transduction system be, a tight regulation of the functioning Rep78/68 protein(s) is necessary.

In nonviral transduction systems, it would be necessary to have Rep proteins functioning only for the time required to obtain the integration, in order to avoid any undesired influence on the cell physiology. This is especially true in light of the observation that Rep exerts a cytotoxic-cytostatic effect on cell cultures (Yang et al, 1994). Moreover, a tight control of the Rep activity on target cells might be required as well, in order to eliminate any possible Rep-dependant recombination, subsequent to the, original integration event.

In the construction of hybrid viral vectors such as adenovirus vectors (Ad)/AAV, i.e. Ad vectors comprising the rep68/78 coding sequence, the AAV ITR and a transgene (with its regulating sequence) among the AAV ITRs, the regulation of Rep activity is required for at least two reasons. Firstly, it is known that Rep can suppress the growth of many viruses, like SV40, HIV, herpesvirus, and Adenovirus. In this last case, particularly, the Rep capacity of inhibiting Ad growth was exhaustively characterised: therefore, in order to generate hybrid Ad/AAV viruses it is necessary to specifically restrain Rep activity on the cell line wherein the adenoviral vector packaging takes place (293 cells derivated from human embryo kidney), otherwise virus yield would be significantly lowered. Whatever be the hybrid virus constructed, in the cell line wherein the packaging takes place Rep activity must be kept low, also to maintain the integrity of the vector genome. As a matter of fact, if it were active during the virus growth, Rep by interaction with the AAV ITRs could promote the transgene excision (and possibly its replication, as it is known that the AAV ITRs may function as replication origin of the eucaryotic cells) off the hybrid vector genome, therefore generating non homogeneous viral populations. On the contrary, obviously, Rep78 and/or Rep68 must be active inside target cells for the time needed to promote the site-specific integration of the desired transgene on the aavsl site.

All these considerations point out that the generation of Rep proteins 78/68, depending for their activity on a ligand added from the outside, would be extremely useful in the field of the somatic gene therapy.

In particular, as the AAV virus most commonly used in gene therapy is the AAV virus of type-2 (AAV-2), applying such a generation of dependant Rep proteins on this specific AAV type virus, would be even more extremely useful.

SUMMARY OF THE INVENTION

The subject matter of the present invention are the hormone-dependant forms of the Rep proteins 78 and Rep 68 of the Adeno-associated virus (AAV), obtained by the fusion of their specific mutants with the hormone binding domain (HBD) of steroid hormone receptors, and the DNA sequences coding for them. These mutant forms in fact enable to obtain a system for the regulation at the post-translational level of the activity of Adeno-associated virus (AAV) Rep proteins by the deletion of the sequence responsible of their localisation in the nucleus (nuclear localisation signal-NLS) and the fusion of the truncated protein with the HBD.

A main discovery which the present invention is based on, consists in the impossibility of regulating the activity of the native proteins Rep 68 and 78. Actually, both Rep 68 and Rep 78 share the same NLS. The whole wild type proteins Rep 68 and Rep 78, in fact, are not regulated by fusion with HBD for steroid hormone, as to both intracellular localisation and the capacity of promoting site-specific integration, because of the presence of this co-shared region. As a consequence, was developed and will be disclosed hereinafter a method object of the present invention by which the Rep protein, truncated in the carboxy-terminal region so as to present a partial or total NLS deletion, becomes subjected to regulation, with the fusion with HBD for steroid hormone.

The partial or total inactivation of the NLS localised in a region embracing the amino acids 480–520 of the Rep proteins 68 or Rep78 primary sequence, can be obtained by different mutations, the most effective being the one consisting in the deletion of the whole domain or of parts of it.

More specifically, the capability of the Rep proteins 68 or 78, deleted from amino acid 505 to amino acid 520, of promoting site-specific integration, can be regulated by fusion with HBD for steroid hormone.

Preferably, the propriety of being regulated by fusion with HBD is obtained by the deletion of the amino acids 492–520, and more preferably by the deletion of the amino acids 485–520.

The regulation of the capacity to promote the site-specific integration of the mutant rep peptides, could be reached by the fusion both at the amino- end and at the carboxy-terminal end of the rep mutants with the HDB for steroid hormones, preferably the regulation of activity of the mutant rep peptides is reached by fusion of the carboxy-terminal end of the mutant rep peptides with the HBD for steroid hormones.

Preferably the HBD utilised is that of the receptor for human progesterone comprising amino acids 640–933 (hPR-HBD)and even more preferably one of its mutants, derivated by the deletion of the C-terminal 42 amino acids, therefore consisting of the amino acids 640–891 (PR891).

In the light of the aforementioned and of what shall be exposed hereinafter, subject matter of the present invention are muteins of the Rep proteins 68 or Rep 78 of an Adeno-associated virus, comprising at least one mutation in a region comprised from residue 480 to residue 520, said mutation being capable of partially or totally inactivating the nuclear localisation signal, being optionally present the wild type Rep 68 or Rep 78 sequence from residue 521 to the carboxy-terminus, said mutein being fused with the binding domain for a steroid hormone.

Particularly, the cases are considered wherein said mutein derives from the wild type protein by the deletion of at least one amino acid of the region comprised from amino acid 480 to amino acid 520. Furthermore, cases wherein the deletion comprises residues 485–520, 492–520 and 505–520, and cases wherein, there existing one of the aforementioned deletions, the region from amino acid 521 to the carboxy-terminus of the sequence of wild type Rep 68 or Rep 78 is absent, are of particular relevance.

A further subject of the present invention are the cases wherein the binding domain for the steroid hormone is situated at the carboxy-terminal end of the Rep 68 or Rep 78 mutein, and is selected from the group comprising the hormone binding domain of the progestinic receptors, the hormone binding domain of the estrogen receptors, the hormone binding domain of the glucocorticoid receptors, the hormone binding domain of the mineralcorticoid receptors, and muteins derivated thereof, particularly the ones wherein said receptors and said hormones are of mammal origin, and particularly that wherein they are of human origin.

Further particular cases are the muteins wherein: the binding domain of the receptor for the progesterone consists in the sequence of amino acids from the residue 640 to the residue 933, in particular said domain is mutated for deletion of the 42 C-terminal amino acids, and consists of the amino acids 640–891; the binding domain for a steroid hormone is situated at the carboxy-terminus of the Rep 68 or Rep 78 mutein.

The present invention further refers to a mutein of the Rep proteins 68 or 78 of an Adeno-associated virus, comprising at least one mutation in a region comprising amino acids from residue 485 to residue 520, and those mutations wherein, there being one of the aforementioned deletions, the region from amino acids 521 to the carboxy-terminal end of the sequence from wild type Rep 68 or Rep 78 is absent.

Moreover, of particular relevance is the case wherein the mutein comprises at least one mutation in a region from residue 480 to residue 520, being optionally present the sequence of wild type Rep 68 or Rep 78 from residue 521 to the carboxy-terminal end.

More particularly relevant is the case wherein the Adeno-associated virus is the Adeno-associated virus of type 2.

The present invention also refers to the DNA sequences, in particular cDNA, coding for the aforementioned muteins, and vectors comprising them, viral or plasmidic, with particular reference to vectors comprising sequences described in the text or in the examples; as RepΔN-P, Rep1ΔN/Pn and Rep1ΔN/P.

Moreover, a further subject of the present invention is a method for regulating the intracellular activity of the Rep 68 or Rep 78 polypeptides of an Adeno-associated virus, essentially comprising a combination of the following steps:

a) introducing in a cell the DNA sequence coding for at least a Rep 68 or 78 protein as previously described, having the nuclear localisation signal (NLS) partially or totally inactive, said DNA sequence being operatively linked to a sequence coding for a steroid HDB, or a derivative thereof;

b) adding a steroid hormone or analogs of the steroid hormone capable to bind said binding domain.

Particular relevance has the cases wherein said DNA sequence codes for the muteins as previously described and is inserted into the cell by viral vector infection, in particular the vectors previously described, or with a transfer technique of the selected DNA from the group comprising electroporing, DEAE-dextran transfection, calcium-phosphate transfection, DNA gun, and liposome-mediated genic transduction.

A further relevant case is that wherein the binding domain of the steps a) and b) are those previously described.

A similar method for regulating the intracellular activity of polypeptides Rep 68 or Rep 78 of an Adeno-associated virus, comprising essentially a combination of the following steps:

A) introducing into a cell a mutein of a Rep 68 or 78 protein having a nuclear localisation signal (NLS) partially or totally inactive, fused to a sequence coding for a binding domain for a steroid hormone or a derivative thereof;

B) adding a steroid hormone or a steroid hormone analogous substance capable to bind said binding domain.

In this method any one of the muteins described herein may be used.

Particularly, the case is considered wherein the regulating method of the intracellular activity of the polypeptides Rep 68 or Rep 78 is applied to eucaryotic cells, preferably mammalian, and most preferably human. A particular case illustrated is the use of 293 cells.

In a preferred embodiment the mutein can be inserted into the cell by liposomes.

The invention will be better clarified with the aid of the annexed figures.

DESCRIPTION OF THE FIGURES

FIG. 3 shows the schematic representation of rep68/78 muteins RepΔC-520, RepΔC-504, RepΔC-491, and RepΔC-484, obtained by deletions in the C-terminal region. The C-terminal sequence of these rep6878 muteins are presented as SEQ ID NOs:12–14; N1, N2 and N3 identify regions of the nuclear localisation domain.

FIG. 8 shows the schematic representation of various fusion proteins obtained by rep68 and rep 78 muteins by fusion with progesterone HBD where the junction sequences of the fusion proteins RepΔN-P, Rep1ΔN/Pn, and Rep1ΔN/P are presented as SEQ ID NO:15, SEQ ID NO:16, and SEQ ID NO:17, respectively.

DETAILED DESCRIPTION OF THE INVENTION

Figure 1:
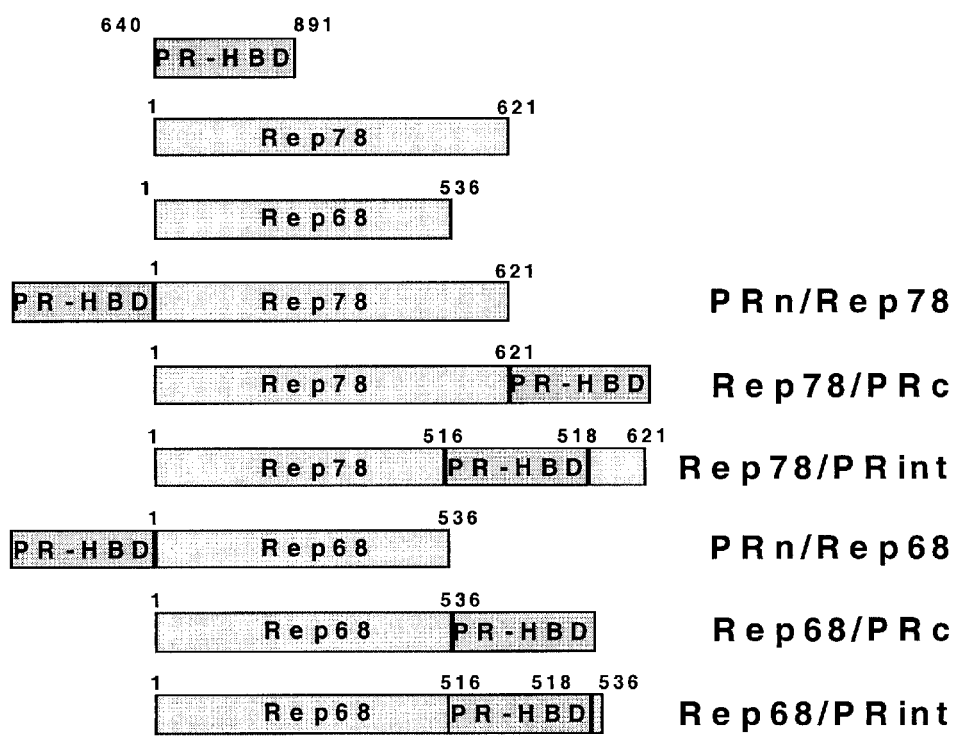
FIG. 1 shows the schematic representation of various fusion proteins obtained from rep68 and rep 78 by fusion with progesterone HBD.

As the Adeno-Associated virus of type 2 is the most commonly used in gene therapy, the invention will be further discussed making specific reference to such preferred application.

The combination of AAV-2 Rep peptides and vectors (both viral and nonviral) carrying a therapeutic transgene flanked by the AAV-2 ITRs can be in fact utilised in the field of the somatic gene therapy. The grounding of this utilisation is based on the notion that Rep peptides 68/78 of AAV-2 can mediate the site-specific integration of a DNA cassette flanked by ITR, both ex vivo and in vivo. The transgene-containing cassette flanked by ITR could be transduced in cells expressing Rep peptides of AAV-2 by recombinant viruses or by forming nonviral particles like liposomes o peptide fragments. Those vectors can be administered to a patient in vivo or ex vivo, to obtain the integration of the desired gene inside a target cell. Thus, utilising this strategy, the defect or genetic deficiency can be stably corrected.

The aim of this work is of making possible the exploitation of the capability of AAV-2 Rep peptides of inserting selected sequences of AAV-2 flanked by ITRs on the integration site aavsl located on human chromosome 19. It is expected that the insertion of therapeutic genes into a defined site of the human genoma will prolong the persistence and the expression of the gene of interest, thereby reducing the risk of insertional mutagenesis.

The present invention refers to the development of regulatory systems of the fusion proteins Rep78/68 activity at a post-translational level. This approach is based on the observation that the binding domain of the receptors of the steroid hormone (HBD) can be used as an autonomous regulation cassette in order to put many heterologous proteins under hormonal control in cis (WO 93/23431). In absence of the hormone the fusion proteins are kept in an inactive state and are rapidly activated by the hormone adding. It has been hypothesised, and in some cases proved, that the inactivation of the functions, inside a heterologous structure of a fusion protein by the non-ligand hormone binding domain, is mediated by a complex containing heat-shock protein 90 (HSP90). The hormone binding causes the release of the HSP90 complex and the protein activation (or derepression). The inactivation of the hormone-reversible protein therefore could work by at least two mechanisms: on one hand, by a relatively a specific mechanism involving the steric hindrance enacted by the HSP90 complex. This method should therefore apply to any protein whose functions are sensible to the steric hindrance enacted by HSP90. On the other hand, for the nuclear proteins sometimes a second level of regulation is operating: actually, as HSP90 is a protein mainly located in cytoplasm, heterologous proteins, usually located inside of the cell nucleus, when fused with the binding domain of the hormone, will be sequestered in cytoplasm: only the addition of the specific ligand will cause the fusion product to be released by the complex with HSP90, thereby allowing the fusion product to freely enter the nucleus.

Therefore, this regulatory system ought to work in the cytosol and nuclear compartment of any organism possessing the components of the HSP90 complex.

The present invention refers to the construction of Rep 78/68 proteins fused to the binding domain of the steroid hormone receptors that depend on the hormone for their activity. Examples are provided with mutants by deletion at the carboxy-terminal end of the hormone binding domain of the receptor of human progesterone (hPR) (WO 93/23431), but on principle the results can be extended to any HBD of any steroid hormone receptor. Particularly, the mutant for HBD deletion at the carboxy-terminal end of the receptor for human progesterone is that leading to a deletion comprising amino acids 630–891 of the hPR. This hormone binding domain does not bind the progesterone anymore, but instead its synthesised analogs), as RU486 (mifepristone), that usually act as antagonists of the progesterone. This mutant form of the binding domain of the hPR hormone will be hereinafter called PR891.

The invention is partially based on the observation that the complete Rep78 and Rep68 proteins, when fused to PR891, could also be not regulated by RU486 with respect both to intracellular localisation and to capacity of promoting site-specific integration of a transgene flanked by AAV-2 ITRs (integration cassette). This was proved true regardless of the fact that the hormone binding domain had been cloned to the carboxy-terminal end, to the amino-terminal end or at the co-shared splicing site level of Rep78 or Rep68. This was attributed to the presence, in the context of Rep78 and Rep68, of a strong NLS located in a region comprising amino acids 480–520 of the primary sequence or the Rep proteins 78/68. Moreover, we hypothesised that a stricter control of Rep 78/68 activity might be reached by the creation of shorter Rep 78/68 versions, maintaining all the functions of the whole proteins, that when fused to PR891 might more easily be subject to steric hindrance by the HSP90 complex in absence of the hormone.

The present invention refers to the generating of Rep mutants with the aim of: 1) identifying the minimal Rep78/68 region maintaining all known functional activities of the natural proteins; 2) dissecting the NLS of Rep78/68; 3) combining those two groups of information for the construction of fusion proteins, constituted by Rep78/68 mutants fused with the hormone binding domain of the receptors for steroid hormones, whose activity is regulated by the addition of the appropriate ligand.

Therefore, the present invention also refers to mutants by deletion of the C-terminal end of the Rep78/68 protein, containing progressive deletions in the NLS.

The present invention also refers to chimerical proteins constituted of mutants by deletion of the carboxy-terminal end of Rep78/68, fused to different portions of the PR891, whose activity is modulated by PR antagonists such as RU486.

The present invention also refers to chimerical proteins constituted by Rep 78/68 proteins containing mutations in the NLS and fused to different portions of the PR891, whose activity is modulated by PR antagonists such as RU486.

The present invention also refers to the construction of expression vectors for Rep78/68, Rep 78/68 mutants and Rep 78/68 mutants fused to PR891.

In a preferred embodiment of the present invention the Rep/PR891 fusion proteins are inserted into culture cells using the calcium-phosphate technique. However, it is immediately evident to a man skilled in the art that the same proteins might be delivered to the cells ex vivo and in vivo utilising any other alternative delivery system, such as those utilising liposomes, condensing agents, DNA and viral vectors.

It will be immediately evident to a man skilled in the art that various substitutions and modifications might be applied to the herein described invention without departing from the scope of the invention. Particularly there is no theoretical objection to using the hormone binding domain of different receptors for steroid hormones (progestinic receptors, estrogen receptors, glucocorticoid receptors, etc.) to regulate the Rep78/68 activity. Moreover, the hormone binding domain of non human steroid receptors can be utilised.

The present invention also provides an in vivo system for the replication and the packaging of Recombinant DNA inside mature virions. Viral preparations containing recombinant DNA incapsidized inside mature virions, obtained by the herein described methods, can be utilised to transfer genetic information inside any cell or tissue of interest.

MATERIALS AND METHODS
Plasmids Construction

As a first step towards the construction of Rep expression vectors and the construction of Rep mutants, the regions coding for Rep, Rep78 and Rep68 were inserted inside the pBluescript II SK (+)plasmid.

The entire rep reading frame, coding for all four the Rep proteins (Rep78, Rep68, Rep52 and Rep40) was amplified by Polymerase Chain Reaction utilising the plasmid psub201, containing the entire AAV-2 genoma (Samulski et al, 1987) as template and the oligonucleotides reported in the annexed sequence listing as SEQ ID NO:1 and SEQ ID NO:2 as direct and inverse primers, respectively. The amplified fragment was digested with the BglII enzyme and inserted into a single BamHI restriction site under the transcriptional control of the T7 promoter, thus obtaining the BS/T7/Rep plasmid. The entire sequence from nucleotide 321 to nucleotide 2252 of the AAV-2 genoma as contained in psub201 was tested by DNA sequencing method utilising a Sequenase sequencing kit (USB). The portion coding for rep was therefore excised from BS/Rep T7 as a 5' SmaI-3'-XbaI fragment, and inserted into a pcDNAIII vector (Invitrogen), digested with EcoRV-XbaI, under the control of the promoter/enhancer of the CMV. This plasmid was called pcRep.

The BS/T7/Rep78 plasmid contains the cDNA coding uniquely for Rep78. It was obtained substituting the ATG codon, in the 993–995 position coding for the initial methionine of the Rep 52/40 proteins, with a GGA codon that codes for a glycine; moreover, the splicing site of the donor was eliminated by the introduction of an A base substituting the G base at nucleotide 1907 of the Rep reading frame contained in psub201. The BS/T7/Rep68 plasmid contains the cDNA coding only for Rep68. It was constructed substituting a SfiI-XbaI fragment coding for the carboxy-terminal region of Rep68 and derivated from pKEX68 (Hörer et al., J. Virol., 69, 5485–5496, 1995) with the corresponding SfiI-XbaI fragment of BS/RepT7. Therefore, this sequence codes for the M225G substitution, as for BS/T7/Rep78 and for the amino acidic ADRLARGHSL-Stop sequence SEQ ID NO:18 at its carboxy-terminal end from amino acid 527 to the stop codon. In order to obtain expression vectors for Rep78 and Rep68, the coding region for Rep78 and Rep68 was excised from BS/T7/Rep78 and BS/T7/Rep68, respectively, as 5'-SmaI/3'-XbaI fragments, and cloned inside expression vector pcDNAIII (Invitrogen), digested with 5'-EcoR/3'-XbaI, under the control of the CMV promoter/enhancer. Those two plasmids were called pcRep78 and pcRep68.

The carboxy-terminal deletions of Rep78/68 (pRepΔ C-484, pRepΔC-491, pRepΔC-502, pReΔC-520) were derivated from pRep68 by stop codon insertions in different positions by PCR strategy. To generate all PCR fragments a primer was used common to 5' the oligonucleotide reported in the annexed sequence listing as SEQ ID NO: 3 (that comprises nucleotides from 1000 to 1022 according to the AAV-2 sequence as filed in GenEMBL database, code number J01901) for all constructs. This oligonucleotide is in position 5' compared to the single BstEII restriction site present in the 1700–1707 position of the AAV-2 sequence as filed in GenEMBL database, code number J01901. For each mutant a specific probe was utilised at 3' inserting an artificial stop codon followed by a restriction site XbaI in the desired position. This strategy enabled to generate for each mutant a PCR fragment that could have been used, after BstEII-XbaI restriction, as a substitute for the BstEII-XbaI fragment to the pRep68 carboxy-terminal end. The specific probes utilised at 3' pReΔ484, pReΔ491, pReΔ502 and pReΔ520 are disclosed in the annexed sequence listing as SEQ ID NO: 4, SEQ ID NO: 5, SEQ ID NO: 6, and SEQ ID NO: 7.

All sequences were confirmed by dideoxyi sequencing carried out with the Sequenase DNA sequencing kit (USB).

In order to construct the ReΔN-P fusion protein, the hormone binding domain of the hPR (comprising amino acids 640–891) was amplified by PCR utilising the appropriate oligonucleotides and utilising the plasmid pT7bhPRB-891 as template. The PCR fragment was cloned as 5'-EcoRI/3'-XhoI fragment in phase with the cDNA coding for ReΔC-484, that was similarly restricted in the plasmid BS/ReΔ484 context. The obtained plasmid was called BS/ReΔN-P.

Finally, the entire reading frame coding for ReΔN-P was excised from plasmid BS/ReΔN-P as SmaI-XhoI fragment and inserted inside expression vector pcDNAIII restricted 5'-EcoRV/3'-XhoI, thus obtaining plasmid pcReΔN-P.

Plasmids containing the cDNA coding for the fusion protein RepΔN/Pn were obtained as follows. Firstly, the cDNA coding for ReΔC-491 was inserted into the plasmid BSΔXhoI. The stop codon was therefore eliminated, and substituted with a XhoI site, by PCR-based mutagenesis, thus generating the plasmid BS/ReΔ49Δstop. Then, a PCR fragment corresponding to the hormone binding domain of the hPR (comprising residues 639–891) was obtained utilising appropriate specific probes and utilising the plasmid pT7bhPRB-891 as template. Then, this fragment was digested at its 5' terminus with XhoI and at 3' terminus with XbaI and inserted in phase with the Rep491 3' terminus in plasmid BS/ReΔ49Δstop restricted with the same two enzymes. The obtained plasmid was called BS/RepΔN/Pn. Finally, the entire reading frame coding for RepΔN/Pn was excised from plasmid BS/RepΔN/Pn as fragment SmaI-XhoI and inserted inside the expressing vector pcDNAIII (Invitrogen) restricted 5'-EcoRV/3'-XhoI, thus obtaining plasmid pcRepΔN/Pn.

Plasmids containing cDNA coding for RepΔN-P fusion protein were obtained by a strategy identical to that followed for RepΔN/Pn, the only difference being that the hormone binding domain obtained by PCR embraces the region from amino acid 642 to amino acid 841. In this case as well, the entire RepΔN-P reading frame was excised from plasmid BS/RepΔN-P as SmaI-XhoI fragment and inserted into the expression vector pcDNAIII (Invitrogen) restricted 5'-EcoRV/3'-XhoI, thus obtaining plasmid pcRepΔN-P.

To obtain the expressing vector coding for Rep78 fused at its carboxy-terminus with the truncated form of the hormone binding domain of human PR the following strategy was adopted. First of all a plasmid BS/Rep7Δ Stop was constructed substituting the BS/T7/Rep78 plasmid stop codon with a XbaI site by PCR strategy. Then, binding domains of the hPR hormone (from amino acid 640 to amino acid 891) were amplified utilising appropriate specific probes by PCR reaction, utilising the pT7bhPRB-891 plasmid (containing the reading frame of human progesterone receptor from amino acid 1 to amino acid 891). The obtained fragment was digested at 5' terminus with XbaI and at 3' terminus with EclXI, and cloned in phase to 3' terminus of the Rep78 reading frame in plasmid BS/T7/Rep78, thus obtaining the plasmid BS/Rep78/PRc containing the cDNA coding for Rep78 fused at its carboxy-terminus with the hormone binding domain (Rep78/PRc). cDNA for Rep78/PRc was excised from BS/Rep78/PRc by digestion with SmaI and NotI subcloned into the pcDNAIII vector restricted 5'-EcoRV/3'-NotI, thus obtaining the plasmid pcRep78/PRc.

To obtain the expressing vector coding for Rep68 fused at its carboxy-terminus with the truncated form of the binding domain of the human PR hormone the following strategy was adopted. Firstly, XhoI site was removed from plasmid pBluescript II SK (+), thus obtaining plasmid BSΔXhoI. The Rep68 coding region was inserted into this vector, and the plasmid BSΔ XhoI/T7/Rep68 was generated. Therefore, the binding domain of the hPR hormone (from amino acid 640 to amino acid 891) was amplified by PCR reaction utilising appropriate specific probes and inserted as 5'-XhoI and 3'-XbaI fragments in phase with Rep68 3' terminus of the reading frame in the context of plasmid BSΔ XhoI/T7/Rep68 previously digested with the same two enzymes. The obtained plasmid was called BS/Rep68/PRc.

The cDNA coding for Rep68 fused at its carboxy-terminus with the 640–891 region of the binding domain of the hPR hormone was therefore excised from BS/Rep68/PRc as 5'SmaI/3'-XbaI fragment and inserted into the vector pcDNAIII, previously digested with EcoRV and XbaI. The obtained plasmid was called pcRep68/PRC.

To obtain the expressing vector coding for Rep78 and Rep68 fused with the hormone binding domain at splicing site level, the following strategy was adopted. In both cases, the hormone binding domain was inserted inside of an AatII natural site (NT 1868–1873) present in the reading frame of Rep78 and Rep68. The hormone binding domain(from amino acid 640 to amino acid 891) was obtained by PCR reaction, again utilising as template plasmid pT7bhPRB-891, digested with AatII and cloned in phase with the Rep78 and Rep68 reading frame, at AatII site of BS/T7/Rep78 and BS/T7/Rep68 thus generating plasmid BS/Rep78/PRint and BS/Rep68/PRint, that contain cDNAs coding for Rep78 and Rep68 fused at the level of the splicing site with the binding domain of the hormone. cDNAs coding for both fusion products were inserted as 5'-SmaI/3'-XbaI fragments inside of the vector pcDNAIII, previously digested with EcoRV and XbaI. Obtained plasmids were called pcRep78/PRint and pcRep78/PRint, respectively.

To obtain the expressing vector coding for Rep78 and Rep68 fused at their N-terminus with the truncated form of the hormone binding domain of the human progesterone receptor, the following strategy was adopted. As a first step, the start codon ATG was removed from plasmid BS/T7/Rep and replaced with a SmaI site, thus obtaining plasmid BS/T7/ReΔATG. Therefore, a hormone binding domain was obtained by PCR, constituted of a methionine followed by the 640–891 region of the hormone binding domain of the human progesterone receptor, utilising the appropriate oligonucleotides on template plasmid pT7bhPRB-891. This met-HBD was cloned as a digested fragment of 5'-ClaL/3'-SmaI, priorly and in phase with the 5' of the Rep reading frame in plasmid BS/T7/ReΔATG, thus obtaining plasmid BS/T7/PR-Rep. Finally, the carboxy-terminal region of the Rep reading frame was excised as 5'-BamHI/3'-XbaI fragment from BS/T7/PR-Rep and replaced with the Rep78 or Rep68 carboxy-terminus region obtained as a similarly restricted 5'-BamHI/3'-XbaI fragment derivated either from BS/T7/Rep78 or from BS/T7/Rep68. Obtained plasmids were called BS/T7/PR-Rep78 and BS/T7/PR-Rep68, respectively.

The corresponding expression vectors, i.e. pcPRn/Rep78 and pcPRn/Rep68 were obtained cloning cDNAs coding for Rep78 and Rep68 fused at their amino-terminus with met-HBD, as 5'-EcoRV/3'-XbaI fragments from BS/T7/PR-Rep78 and BS/T7/PR-Rep68, respectively, inside of a similarly restricted pcDNAIII expression vector (Invitrogen).

In vitro Translation

In vitro translated Rep polypeptides were synthesised from plasmids derivated from pcDNAIII utilising the TNT/T7 system associated with reticulocyte lysate (Promega) following the manufacturer's instructions. The protein synthesis and the radioactive marking were performed with 1 µg plasmidic DNA for 2 hours at 30° C. in presence of 40 µCi L-$^{35}$S methionine. Rep proteins underwent electrophoresis on a 8% SDS-polyacrylamide gel and were detected by autoradiography. To normalise the amount of wild type Rep78/68 and the Rep mutants utilised in the various comparative assays of binding to DNA and endonuclease, the relative concentration of the various Rep proteins was determined by gel densitometric reading, carried out utilising Phosphorimager (Molecular Dynamics).

Electrophoretic Mobility Shift Assay

The assays of electrophoretic mobility shift were carried out with 20000 cpm AAV-2-ITR $^{32}$P-labelled at one end. The reaction mixtures were contained in a 10 µl volume, 10 mM Hepes-NaOH pH 7.9, 8 mM $MgCl_2$, 40 mM KCl, 0.2 mM DTT, 1 µg poly (dl-dC), increasing the concentration of in vitro translated proteins.

The DNA binding reactions were incubated at room temperature for 20–30 minutes and seeded, after 4% Ficoll addition, on a 4% polyacrylamide gel containing 0.5 ×TBE.

Assays of trs Endonuclease

The trs endonuclease assays were performed as previously described (D. S. Im and N. Muzyczka Cell 1990, 61, 447–457), utilising substrates similar to ITR with a single-stranded terminal resolution site. Plasmid psub 201 was digested with XbaI and PvuII, treated with calf intestine alkaline phosphatase, and the fragments labelled with polynucleotide kinase at 5' end. The labelled fragments were then purified with electrophoresis on a 6% sequencing gel. The endonuclease reaction mixture contained in a 20 µl volume: 25 mM Hepes-KOH (pH 7.5), 5 mM $MgCl_2$, 0.2 mM EGTA, 1 mM DTT, 0.4 mM ATP, 0.2 µg BSA, 1 µg poly (dl-dC), 10000–20000 cpm of substrate $^{32}$P-labelled at one end, and increasing the concentration of the proteins translated in vitro. The reactions were incubated for 1 hour at 37° C., treated with K proteinase for 30 minutes at 65° C., extracted with phenol/chloroform and precipitated in ethanol. The reaction products were therefore utilised on a 8%.sequencing gel.

Cell Colture and Transfection

The 293 cells were maintained in Dulbecco's modified Eagle's medium (DMEM) supplemented with 10% fetal calf serum, 100 units/ml penicillin and streptomycin, 2 mM glutamine at 37° C. in 5% $CO_2$. The transfection of the 293 cells was carried out by calcium-phosphate precipitation.

Western Blot Analysis

To analyse the expression of Rep, 3×10$^5$ cells were transfected with 10 µg expression plasmid. 48 hours p.t., cells were washed in PBS and lysated in 10 mM Tris-HCl (pH 8.0), 5 mM EDTA, 1% SDS with an 1 ml syringe. The lysate was precipitated with 10% TCA at room temperature for 15 minutes and for 5 minutes in ice. After a 15 minutes 14000 rpm centrifugation, precioitates were washed in 100% cold acetone for 15 minutes, and then at 100° C. for 3 minutes. Proteins were fractionated on an 8% SDS-polyacrylamide gel and transferred on a nitro-cellulose membrane utilising an electrophoretic transfer apparatus.

The membrane was incubated with rabbit polyclonal antiserum directed against AAV-2 Rep proteins, and therefore with secondary anti-rabbit AP-conjugated IgG.

Rescue Replication Assay (RR).

24 hours prior to transfection, $1.2 \times 10^6$ cells were seeded in 10 mm plates and incubated at 37° C. in 5% $CO_2$. 2 hours prior to transfection the cells were infected with Ad2 to a MOI of 10. The transfections were performed by calcium-phosphate precipitation utilising 10 μg of the various expression vectors and 10 μg of a plasmid containing the AAV-2-ITR. 60 hours posttransfection low molecular weight DNA was isolated by Hirt extraction procedure, extensively digested with DpnI and analysed on Southern blotting utilising $^{32}P$-labelled DNA probes, specific for sequences contained among the AAV-2 ITRs.

Immunofluorescence Assay.

To perform immunofluorescence assays Hep3B cells were coltured on slides and transfected as previously described. 36 hours p.t. cells were fixated with 3% formaldehyde in PBS at room temperature for 20 minutes, washed in PBS and incubated in 0.1 M glycine in PBS at room temperature for 10 minutes. To perform intracellular colouring, slides were incubated at room temperature for 5 minutes with 0.1% Triton in PBS. Then cells were washed in PBS, incubated 20 minutes with mouse monoclonal Ab anti-Rep 1:30, in 10% goat serum in PBS, and washed in PBS. After 20 minutes incubation, and with goat antimouse IgG conjugated with secondary rhodamine, cells were washed in PBS and in $H_2O$, and finally put on slides. Subcellular localisation of mutants by Rep carboxy-terminal deletion was visualised utilising rabbit polyclonal antibodies, aimed against AAV-2 Rep (1:200 in 10% goat serum in PBS) and as secondary Ab a fluorescein conjugated with goat anti-rabbit IgG.

PCR Assay for Site-specific Integration.

For each assay, 24 hours prior to transfection $1.2 \times 10^6$ 293 cells were seeded on 10 mm plates and incubated at 37° C. in 5% $CO_2$. Cells were cotransfected by calcium phosphate method with 10 μg of the various expression vectors and with 10 μg of the plasmid bearing ITRs-flanked DNA sequences. 48 hours p.c., the total genomic DNA was extracted and 2 PCR cycles were carried out. The PCR mixture contained in a 50 ml volume, genomic DNA 500 μg, 10 mM Tris-HCl pH 8.3, 50 mM KCl, 2.5 mM $MgCl_2$, 200 mM of each triphosphatic deoxynucleoside, 1.25 U Ampli-Taq Gold Polymerase (Perkin Elmer) and 50 pmoles of each primer. For the second PCR cycle 10 μl of the first cycle were utilised. Conditions were 94° C. for 10 minutes followed by 25 cycles at 94° C. for 1 minute, 60° C. for 1 minute and 62° C. for 2 minutes.

First Cycle Probes:
p1: the oligonlucleotide reported in the sequence listing as SEQ ID NO:8 hybridised at AAV-2 (ITR) nucleotides 4513–4522
p2: the oligonlucleotide reported in the sequence listing as SEQ ID NO:9 hybridised at nucleotides 1322–1342 of the chromosome 19 (AAVS1)

Second Cycle Probes:
p3: the oligonlucleotide reported in the sequence listing as SEQ ID NO:10 hybridised at AAV-2 nucleotides 4533–4559,
p4: the oligonlucleotide reported in the sequence listing as SEQ ID NO:11 hybridised at nucleotides 1169–1194 of the chromosome 19.

PCR products were separated on 1.5% agarose gel, then transferred on filter and hybridised with specific ITR or AAVS1 probes (probe ITR: nucleotides 4563–4670, probe AAVS1: nucleotides 210–1207).

The ends of the PCR reaction positive products were filled in by Klenow polymerase activity, cloned into pBluescript II SK vector and sequenced.

So far, a general description was given of the present invention. With the aid of the examples hereinafter, a more detailed description will now be given of specific embodiments thereof, with the purpose of giving a clearer understanding of objects, features, advantages and methods of application of the invention. These examples are merely illustrative, and do not limit the scope of the present invention, that is defined by the enclosed claims.

EXAMPLE 1

In order to test whether Rep78 and/or Rep 68 may be subject to hormonal regulation following their fusion with the hormone binding domain belonging to a steroid hormone receptor, fusion were generated with the hormone binding domain for the human progesterone receptor (hPR). More specifically, we utilised a form truncated at the carboxy-terminal end of the binding domain of the PR hormone (amino acids 640–891) hPR that does not bind the progesterone, but rather binds and is activated by some of its synthesised analogs such as RU 486, that usually acts as a progesterone antagonist.

Six different fusion proteins, three for Rep78 and three for Rep68 were constructed. Basically, the hormone binding domain was put at the amino-terminal end, at the carboxy-terminal end or at the level of the Rep78 and Rep68 splicing junctions. The schematic structure of the fusion proteins is represented in FIG. 1. cDNAs coding for these chimerical proteins were put inside appropriate expression vectors under the control of the cytomegalovirus (CMV) enhancer/promoter. To test the expression of all fusion products, the corresponding expression vectors were transfected in human 293 cells: 48 hours p.t., total cellular extracts were prepared and analysed by western blotting technique. It is important to stress that most references were performed on 293 cells, because these are the cells for the Ad vectors packaging. Fusion wherein the hormone binding domain was inserted at the carboxy-terminal end or at the level of the Rep78 and Rep68 splicing sites stand out clearly utilising this assay. On the contrary, when the expression vectors for the two N-terminus fusion were transfected in 293 cells, a band of lower than expected molecular mass was spotted. This might indicate that either the protein is unstable, or the translation could start from an internal methionine different from the artificially inserted one. Control experiments showed that the N-terminal fusion of desired dimensions could be produced by in vitro translation experiments utilising the same expression vector transfected in cells. This strongly suggests that the smaller dimension observed in cells is possibly due to the fact that the N-terminus fusion products are partially degraded by intracellular protease.

EXAMPLE 2

Figure 2A:
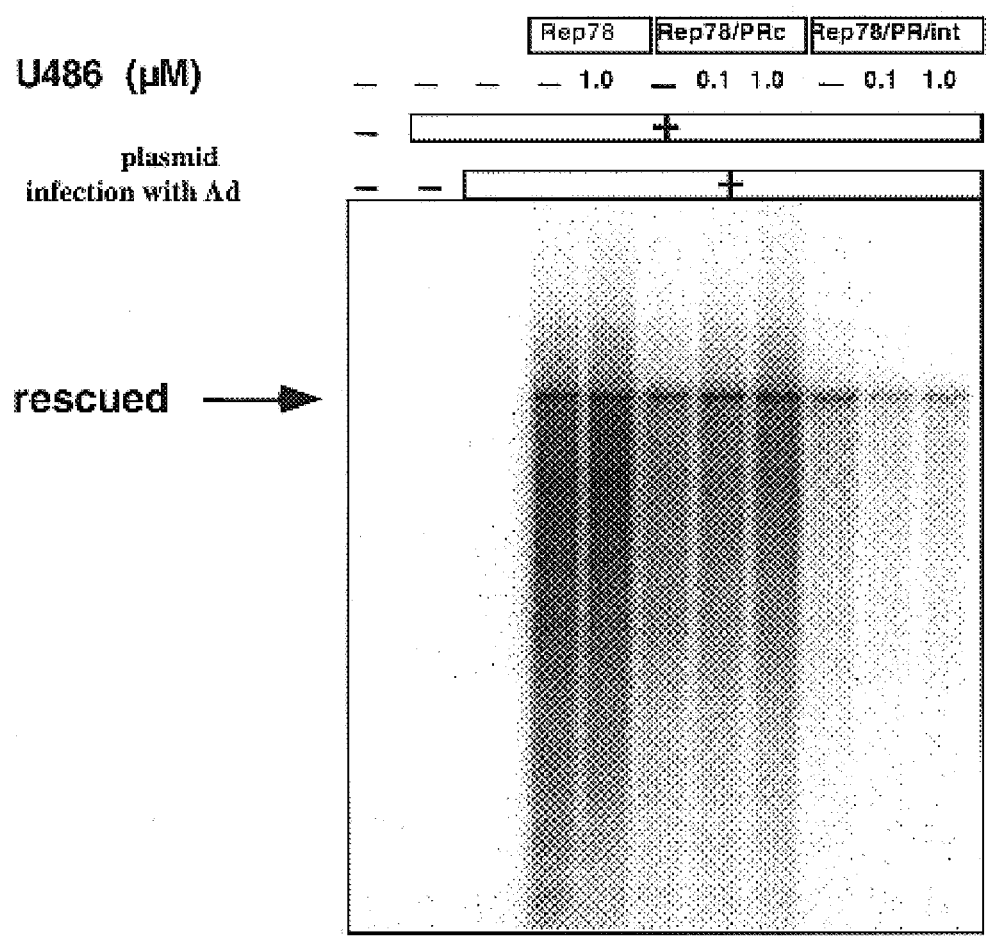
FIG. 2 shows photographs of electrophoretic gels reporting the results of Rescue-replication experiments obtained using various fusion proteins obtained from rep68 and rep 78 by fusion with progesterone HBD.
Figure 2B:
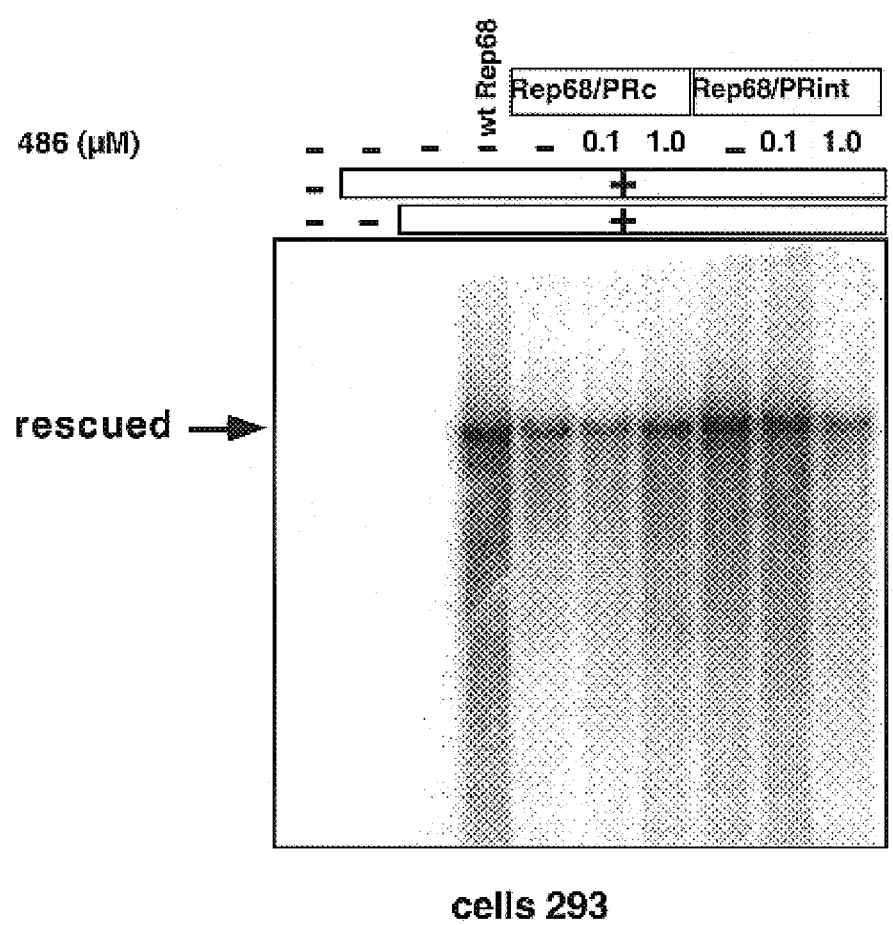

Then it was tested the fusion proteins activity in Rescue-replication assays. It is known that Rep78/68 is capable, in Ad-infected cells, of promoting the freeing from a recombinant plasmid and the replication of each DNA sequence contained among the AAV-2 ITRs (see FIG. 2). To test whether in this assay the activity of the four fusion proteins correctly expressed in cells (Rep78/PRc, Rep68/PRc, Rep78/PRint Rep68/PRint) might have been modulated by RU486 added from the outside, the experiments hereinafter were performed. 10 µg of the various expression vectors were cotransfected in Ad-infected 193 cells, together with 10 µg of the so-called "replication substrate", i.e. a plasmid containing whichever DNA segment (in this specific case sequences coding for beta-galactosidase enzyme (β-Gal) and for Hygromycin resistance gene) located among the AAV-2 ITRs. In control experiments cells were transfected with expression vectors for Rep78 and Rep68. 5 hours p.t., cells were washed and the colture medium changed: for each construct, two plates of transfected cells were treated with 100 mM and 1 µm RU486, while untreated cells were utilised as a control of the basal activity level. 60 hours p.t., low molecular weight DNA was isolated and digested with DpnI restriction enzyme. This enzyme has a far greater activity when both adenosine in the recognition sequence are methylated: as the adenine methyilation of residues is not carried out by eucaryotic methylases, the conversion to DpnI resistance indicates that hemimethylation or the absence of methylation is the result of one or two DNA replication cycles in the eucaryotic host. DpnI- digested DNAs were analysed by southern blots utilising a $^{32}$P-labelled DNA probe specific for b-Gal cDNA. The evaluation of the basal activity level and of the hormonal inducibility with RU486 of the Rep fusion proteins was carried out comparing intensities of the bands corresponding to plasmids replicated in various experimental conditions. Results, shown in FIG. 2, indicate that under these experimental conditions Rep78 and Rep68 fusion proteins possess a quite high basal activity level, not substantially influenced by RU486.

EXAMPLE 3

Figure 4:
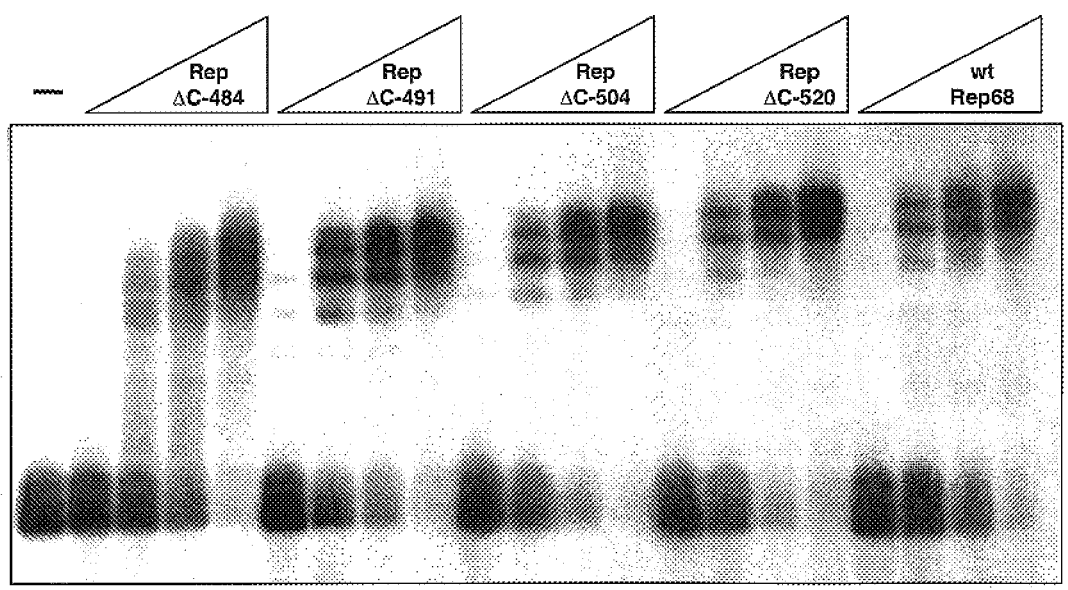
FIG. 4 shows photographs of electrophoretic gels reporting the results of experiments of specific binding of rep68/78 muteins, obtained by deletions in the C-terminal region, with a DNA having their recognition sequence contained within the AAV-2 ITRs.

Then it was decided to test whether fusion proteins were capable of promoting site-specific integration in human chromosome 19 of an ITRs-flanked DNA sequence. This was performed in order to determine whether the presence of the hormone binding domain might negatively influence the Rep78 and Rep68 integration competence. To this end, it was developed a short-term integration assay. Under these experimental conditions, cells are cotransfected with expression vectors for Rep and with a plasmid containing a DNA sequence comprised among the AAV ITRs, in this case sequences coding for Hook antibody (InVitrogen®) and neomycin resistance gene. In control experiments cells are transfected only with integration cassettes. 2 days p.t., cells are harvested, high molecular weight DNA extracted and utilised as template for a PCR reaction utilising primers that ought to flank ITR-aavsl junctions. A first amplification is performed utilising a primer for ITR (nucleotides 4513–4522, right side ITR in the psub201 vector) combined with a specific primer for aavsl region nucleotides 1332–1342. A portion of this amplification product is therefore subject to a second PCR reaction (called nested-PCR) utilising other specific oligonucleotides, both for ITR (nt 4533–4559) and for aavsl (nt 1169–1194), that are internal and therefore different from those previously used. This last amplification product undergoes electrophoresis on agarose gel and is hybridised with aavsl- and ITR-derived probes: signals identified with both probes are considered as deriving from specific amplification of the ITR-aavsl junctions and therefore assessed as events of real site-specific integration. As is shown in FIG. 4, representing a typical experiment, no signal is detected in transfected cells with the integration cassette without Rep; on the contrary, positive signals, i.e. site-specific integration events, are detected with both probes in cells cotransfected with the vector containing the genic cassette flanked by AAV-ITRs and with expression vectors for Rep both 68 and 78. Similar results were obtained in 293 cells, HepG2, Hela and Huh7 (data not shown). The fact that the positive signal appears as a spread on agarose gel, is consistent with the observation that the site-specific integration can occur in a region embracing at least 100 bp of the human chromosome 19, and therefore it is expected that the amplified ITR-aavsl junctions are of heterogeneous dimensions.

EXAMPLE 4

The Rep78/PRc Rep68/PRc, Rep78/PRint, Rep68/PRint integration capacity was tested in short-term integration assays carried out on 293 cells. The obtained results (summarised in table 1), indicate that all fusion products are capable of promoting site-specific integration as determined in this assay. However, also in this case no hormonal control whatsoever was observed.

TABLE 1

| | Site-specific integration | |
|---|---|---|
| | w RU486 (1 µM) | w/o RU486 (1 µM) |
| Rep78 | + | + |
| Rep68 | + | + |
| Rep78/PRC | + | + |
| Rep79/PRint | + | + |
| Rep68/PRc | + | + |
| Rep68/PRint | + | + |

EXAMPLE 5

Nuclear localisation of the fusion proteins was verified by immunofluorescence experiments. As receiving cells, Hep3B cells were selected. Thus, Hep3B cells were transfected with expression vectors for Rep78, Rep68 and their chimerical derivatives: for these latter proteins transfected cells were treated or not with 1 µM RU 486. 36 hours p.t. were fixed under the appropriate conditions and the intracellular Rep distribution was monitored by sequential incubation with rabbit polyclonal antiserum aimed against Rep78/68 and goat anti-rabbit IgG conjugated with fluorescein. The obtained results are summarised in table 2.

TABLE 2

| | RU486 (1 µM) | N > C | N < C | N = C |
|---|---|---|---|---|
| wt Rep68 (78) | − | 95% | 5% | — |
| Rep68/PRc | − | 5% | 90% | 5% |
| Rep68/PRc | + | 90% | 5% | 5% |
| Rep68/PRint | − | 15% | 75% | 10% |
| Rep68/PRint | + | 85% | 15% | — |
| Rep78/PRc | − | 5% | 90% | 5% |
| Rep78/PRc | + | 90% | 5% | 5% |
| Rep78/PRint | − | 35% | 25% | 40% |
| Rep78/PRint | + | 60% | — | 40% |

The results are given as percentages of cells expressing Rep peptides according to the specific phenotype:
  N>C: cells expressing Rep mostly in nucleus;
  N<C: cells expressing Rep mostly in cytoplasm;
  N=C: cells wherein Rep expression does not have a predominant cellular localisation.

From those experiments, some clear-cut conclusions were drawn: 1) as expected, wild type Rep68 and Rep78 are located almost exclusively in nucleus; 2) intracellular localisation of the fusion proteins modulated by RU486; 3) control is stricter for fusion proteins bearing the hormone binding domain at the carboxy-terminus (Rep68/PRc and Rep78/PRc): however, also in this case a low amount of the solution product is present in the nucleus of the untreated cells; 4) Evidence that even in absence of RU486 a low amount of the fusion product is present in the nucleus might at least partly explain why all fusion products possess a strong basal activity both in rescue-replication assay and in integration assay.

EXAMPLE 6

To subject fusion protein Rep78/68 to hormonal controls it was decided to perform Rep78/68 mutagenesis with the aim of: 1) identifying the Rep78/68 minimal region possessing the same activity as the whole protein; 2) accurately mapping the Rep78/68 NLS; 3) to take advantage of information obtained from those two experiments for the construction of hormone-dependant Rep/PR fusion proteins.

Rep78/68 nuclear localisation signal (NLS) was located by other research groups approximately between amino acids 480 and 520. On the basis of this information we constructed four carboxy-terminus deletions of Rep78/68. They were RepΔC-520 (containing the first 520 N-terminal amino acids of Rep78/68), that comprises all putative NLS; RepΔC-502 wherein a first group of positively charged residues is deleted that might constitute part of the NLS; RepΔC-491 wherein a second group of positively charged amino acids is removed and lastly RepΔC-484. Their structure is schematically represented in FIG. 3. It was noted that they can actually be considered as carboxy-terminal deletions of Rep68. cDNAs coding for those mutants were inserted into the appropriate eucaryotic expression vectors and tested in vitro and in vivo.

Regarding the in vitro experiments, four mutants as well as wild type proteins were produced by in vitro translation and therefore assayed for their binding activity to DNA and for endonucleasic activity. Regarding the DNA binding, it was determined the capacity of those mutants in EMSA (Electrophoresis Mobility Shift Assays) to bind a double-stranded oligonucleotide embracing the Rep binding site contained in AAV-2 ITRs. As is shown in FIG. 4, all the RepΔC mutants bound their recognition sequence on DNA in the same manner as wild type Rep68, with the sole exception of RepΔC-484 evidencing a weaker DNA binding activity.

Figure 5:
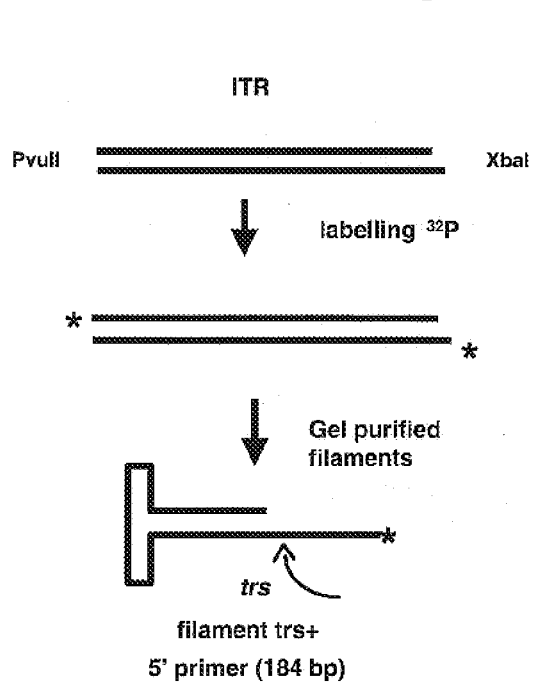
FIG. 5 shows photographs of electrophoretic gels reporting the results of endonucleasic activities experiments of rep68/78 muteins, obtained by deletions in the C-terminal region.
Figure 5:
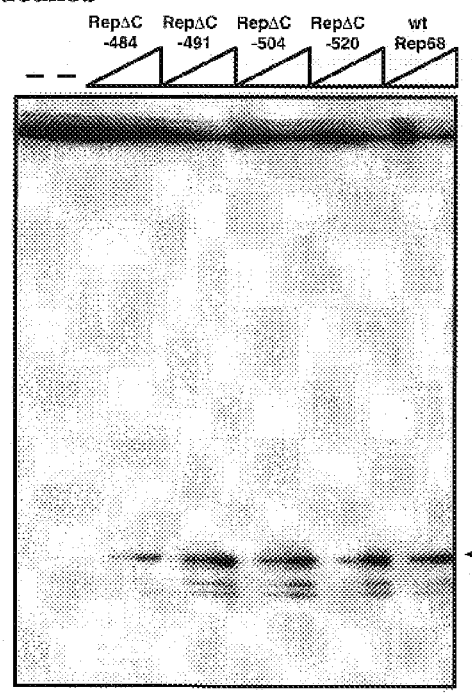

The same mutants were tested for their capacity of cleaving AAV-2 ITRs in a strand- and site-specific way utilising a well-defined assay (see materials and methods). In this case as well, only RepΔC-484 evidenced a weaker (although clearly distinguishable) activity compared to wild type Rep68 (see FIG. 5).

The functional properties of those four mutants were therefore tested in transfected cells. In a first series of experiments, the intracellular localisation of those four deletion mutants was assayed utilising the protocol evidenced supra. Results are summarised in table 3.

TABLE 3

Intracellular localisation of Rep__C mutants

|  | N | C | N = C |
|---|---|---|---|
| wt Rep68 (78) | 95% | — | 5% |
| Rep__C-520 (N1 + N2 + N3) | 95% | — | 5% |
| Rep__C-502 (N1 + N2) | 57% | 1% | 42% |
| Rep__C-491 (N1) | 17% | 42% | 42% |
| Rep__C-482 | — | 100% | — |

As expected, RepΔC-484 was not nucleus-located at all: as for the other mutants, there is a progressive increase in the percentage of transfected cells expressing the protein in the nucleus. RepΔC-491 Mutant is already partially located in nucleus: particularly, in 17% of the transfected cells the protein was located exclusively in nucleus, and in 42% of transfected cells the protein was found both in nucleus and in cytoplasm. With reference to RepΔC-502 mutant, only in 1% of the transfected cells the protein was located exclusively in cytoplasm. RepΔC-520 behaved as wild type Rep68. As a whole those experiments prove that Rep NLS can be functionally subdivided within at least three regions: N1, comprising amino acids 484–491; N2, comprising amino acids 491–502 and N3, comprising amino acids 502–520. It is important to notice that N1 by itself is sufficient to promote the in-nucleus localization of the Rep protein. Moreover the fact must be stressed that the numerical evaluation of the intracellular localisation by immunofluorescence experiments, while very useful for our goals (i.e. mapping the NLS of Rep78/68), is limited by the relative sensibility of the assay: this means that we cannot exclude that in cells considered as negative for their nuclear localisation, undetectable intranuclear Rep levels could actually subsist.

Rep ΔC mutants were therefore assayed in rescue-replication assay, according to the protocol evidenced supra.

Figure 6:
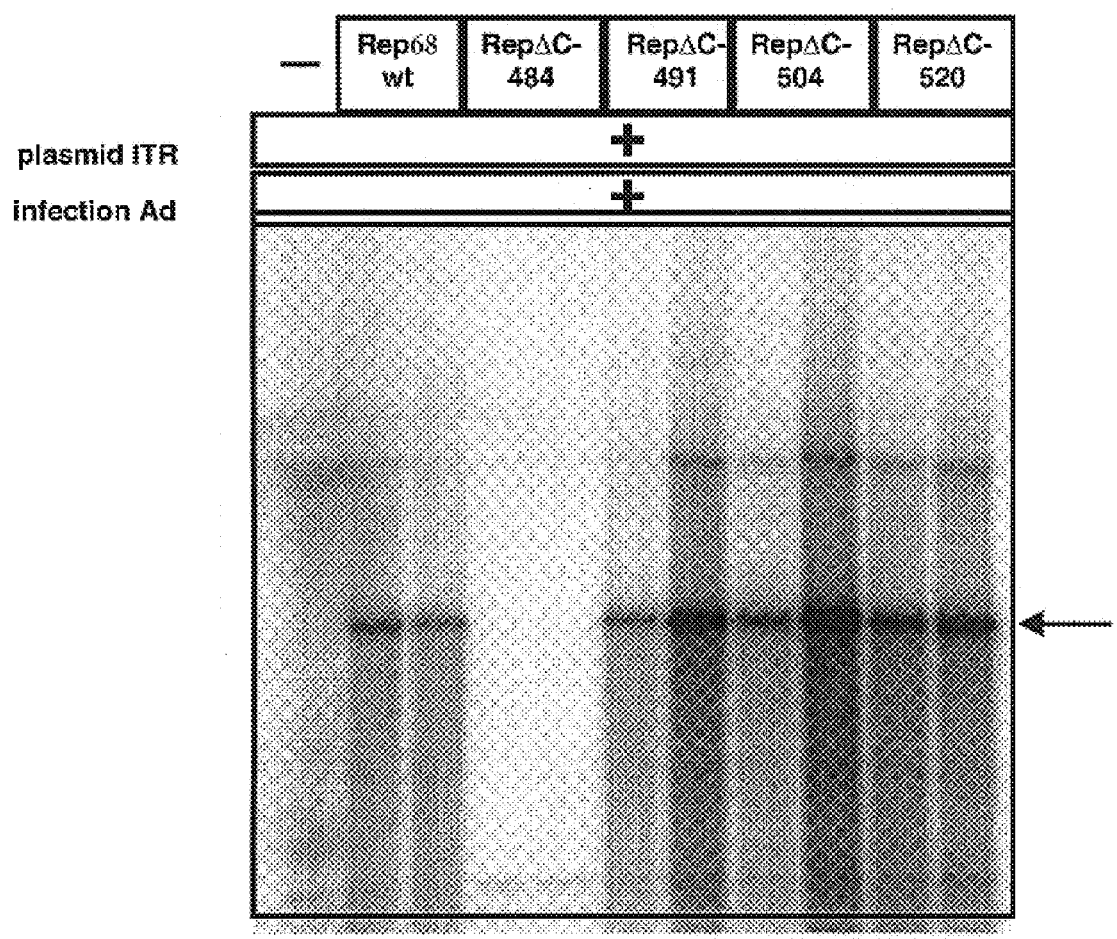
FIG. 6 shows photographs of Southern-blot reporting the results of Rescue-replication experiments of rep68/78 muteins, obtained by deletions in the C-terminal region.

The results are shown in FIG. 6. RepΔC-484 is unable to promote rescue-replication of ITRs-flanked sequences: this result was expected, because it is known that rescue-replication occurs in the cell nucleus, where this mutant is unable to migrate. On the contrary, all other mutants are active as wild type Rep68. The fact that all mutants possessed the same-activity in the rescue-replication assay, regardless of their containing nuclear localisation signals of different strength, is not surprising: actually, it is known that very low levels of intranuclear Rep are still capable of promoting an efficient rescue-replication, and, as evidenced above, the definition of Rep proteins intracellular localisation by immunofluorescence experiments presents some limitations.

Figure 7:
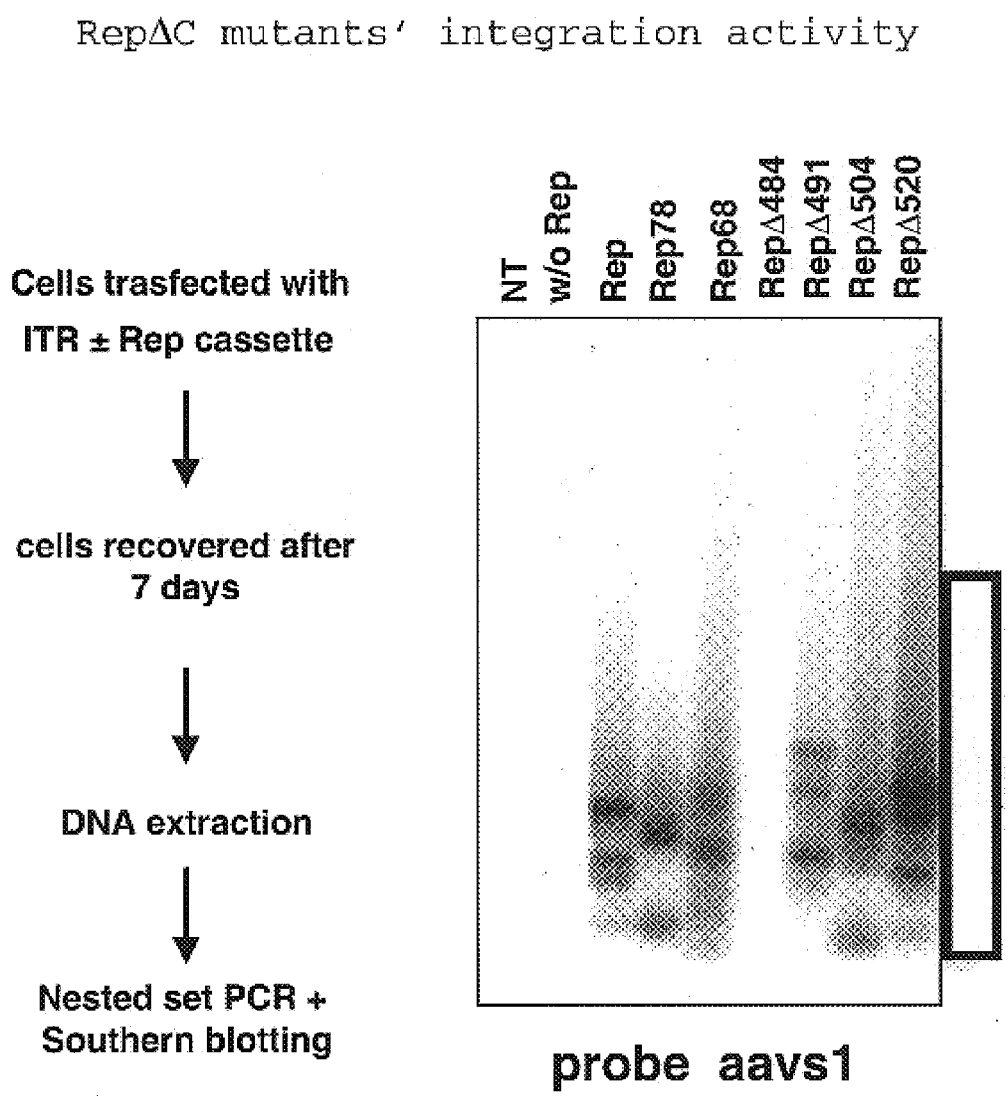
FIG. 7 shows photographs of Southern-blot reporting the results of experiments of integration activity, specifically on aavsl site, mediated by rep68/78 muteins, obtained by deletions in the C-terminal region.

Finally, capacity of RepΔC mutants was verified by short-term integration assays. Results are shown in FIG. 7 where, for the sake of simplicity, only aavsl probe hybridisation is shown. In accordance with expectations all mutants were able to promote site-specific integration with the sole exception of RepΔC484, that does not enter nucleus.

To facilitate data analysis, results obtained in vitro and in vivo with the four RepΔc mutants are summarised in table 4.

To sum up, all those experiments prove that the minimal Rep region containing all the activities of wild type Rep68 is the one embracing the first 491 amino-terminal amino acids (RepΔC-491): this protein possesses the same activity as in vitro Rep68 (binding to DNA and endonucleases activity) and contains a NLS region important from a functional point of view.

EXAMPLE 7

On the basis of the results obtained by mutants by deletion of the carboxy-terminal part, it was decided to construct three further Rep/PR fusion proteins, constituted by different Rep68 deletion mutants fused at the binding domain of the hPR hormone. Particularly, we decided to fuse RepΔC491, the smaller region of Rep68 still maintaining the full activity, and possessing a partially damaged NLS, at the hormone binding domain. It is expected that this may strengthen the hormone dependence of the fusion products with respect to nuclear localisation: moreover, it is expected that the dimensional reduction of the Rep protein may favour the steric hindrance exerted by the hormone binding domain on the fusion product in the ligand absence.

The first fusion was carried out joining the Rep region comprising amino acids 1–491, containing part of the Rep NLS (region N1, see supra), in phase with the hPR region comprising residues from 639 to 891. This mutant was called Rep1ΔN/Pn: a schematic representation of its structure is shown in FIG. 8. In the same figure is indicated that for reasons consequent to clonation, the insertion of two spurious amino acids has been detected, i.e. a leucine residue and a glutamate residue, between the Rep region and the hormone binding domain. Moreover, FIG. 8 shows that the selected region of the hormone binding domain contains two lysine residues (K640 and K641) that were considered as part of one of the three nuclear localisation signals usually present in PR.

The second fusion was carried out joining the Rep region comprising amino acids 1–491, in phase with the hPR region comprising residues from 642 to 891: this last region does not contain lysine residues K640 and K641. This mutant was called Rep1ΔN/P. Its structure is schematically represented in FIG. 8: in this case as well, between the Rep region and the hormone binding domain, there is the insertion of one leucine residue and one of glutamic acid.

A third fusion was carried out utilising RepΔC484: this protein partly maintains the wild type Rep 78/68 activity, with reference to the binding to DNA and endonuclease activity, but has no in vivo activity whatsoever, as it does not possess the nuclear localisation signal. We therefore generated a third fusion joining the Rep region comprising amino acids 1–484, in phase with the hPR region comprising residues from 635 to 891: this last region contains one of the three nuclear localisation signals present in hPR. This mutant was called RepΔN-P. Its structure is schematically represented in FIG. 8: in this case, the Rep coding sequence is joined directly in phase with the hormone binding domain.

Figure 9:
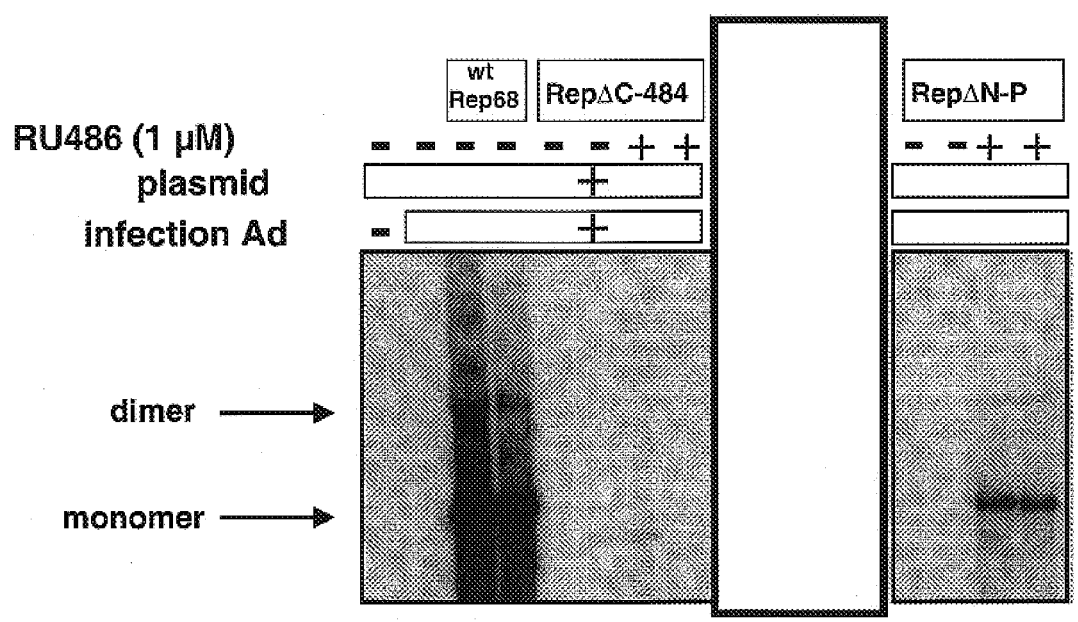
FIG. 9 shows photographs of Southern-blot reporting the results of Rescue-replication experiments, depending on the presence of RU486 with a rep68/78 mutein obtained by deletions in the C-terminal region and the corresponding mutein fused with progesterone HBD.

All of the three fusion were tested with rescue-replication assays performing the transfection of Ad-infected 293 cells with the corresponding expression vectors and the appropriate plasmid substrate. As is shown in FIG. 9, under these experimental conditions RepΔN-P evidenced a full hormone dependence: no activity whatsoever was observed in absence of the hormone, while an evident activation was observed with 1 μM RU486. Different experiments proved this activation to be dose-dependant, with a lesser activity observed at 10 μM RU486 and a plateau level at 10 μM (data not shown). In no case the fusion products activity was as high as that of wild type Rep68: it is believed to be due to the RepΔC-482 low activity.

Figure 10:
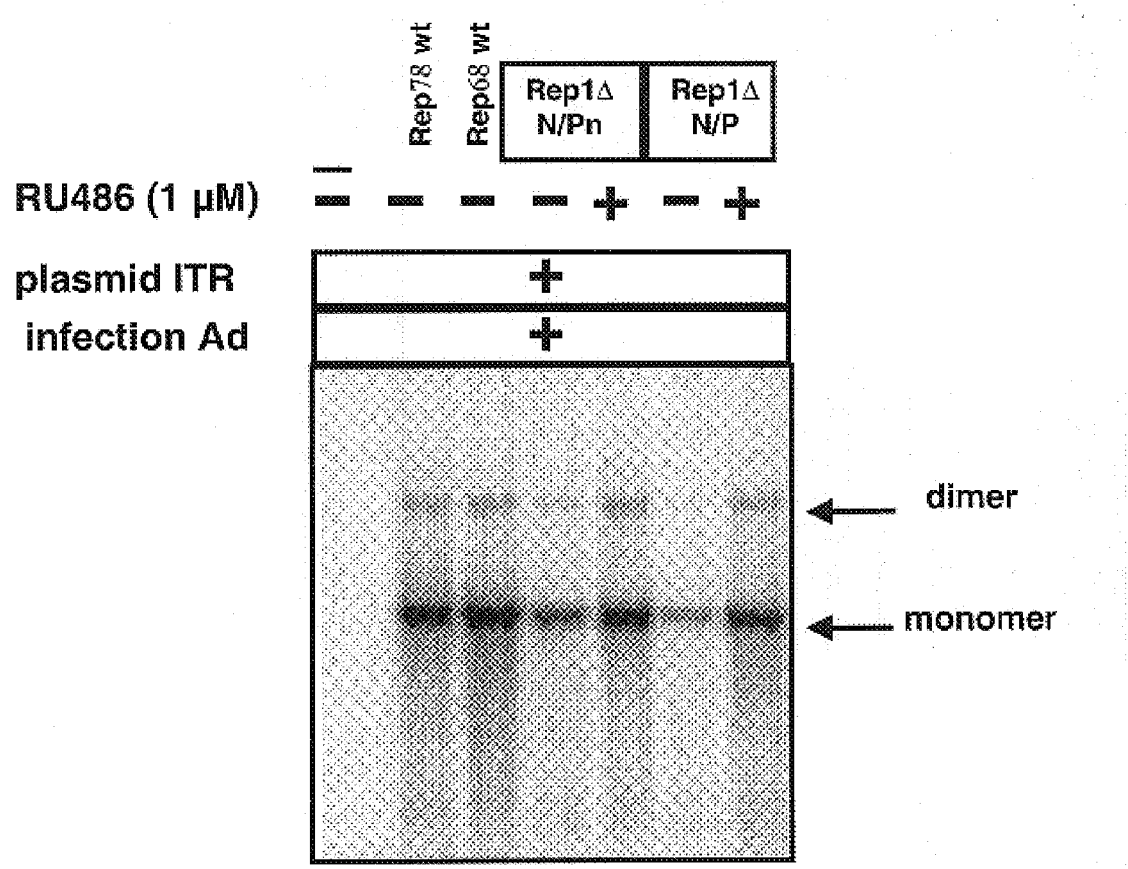
FIG. 10 shows a photograph of Southern-blot reporting the results of Rescue-replication experiments depending on the presence of RU486 with rep68/78 muteins obtained by deletions in the C-terminal region and the corresponding mutein fused with progesterone HBD.

As is shown in FIG. 10, the other two fusion products as well are hormone regulated. In this case, there was basal activity in absence of RU486: however, this activity was markedly intensified by the hormone addition. Interestingly, the control was stricter for RepΔlN/P, wherein the hormone binding domain does not contain any nuclear localisation signal.

Figure 11:
FIG. 11 shows a photograph of Southern-blot reporting the results of site-specific integration experiments, depending on the presence of RU486, mediated by rep68/78 muteins obtained by deletions in the C-terminal region and fused with the progesterone HBD.

The three mutants were finally tested in short-term integration assays carried out in 293 cells as described supra. As is shown in FIG. 11, showing the hybridisation frame with aavsl-derived probes, the fusion product RepΔN-P, derivated from RepΔC484, is incapable of promoting site-specific integration even in presence of RU486. The observation that the RepΔN-P fusion is capable of promoting rescue-replication but not site-specific integration is explained with the higher probability by the fact that rescue-replication (RR) is evidenced from a far more sensible assay. In fact, in RR the initial event, the freeing of the ITR-flanked sequences, is largely amplified by the subsequent replication of the freed fragment.

Interestingly, the other two fusion Rep1ΔN/P and Rep1ΔN/Pn, were both capable of promoting site-specific integration (see FIG. 11). In this case, no signal was observed in absence of the hormone while specific signals were detected in presence of 1 μM RU486. To further test the results validity, we cloned and sequenced two amplified junctions, one for each mutant, that not only cohybridize with aavsl and ITR probes but were also clearly evident after staining with ethidium bromide of agarose gel. The junction sequences obtained for Rep1ΔN/P and Rep1ΔN/Pn are shown in FIG. 8: both are in good accordance with the sequences of the junctions derivated by the AAV-2 infected cells.

To sum up, the obtained results prove that it is possible to construct hormone-dependant Rep78/68 forms by reducing the protein dimensions and the strength of its natural NLS (nuclear localisation signal)

BIBLIOGRAPHY

Balagué, C., M. Kalla, and W.-W-Zhang (1997). Adeno-associated virus Rep 78 protein and terminal repeats enhance integration of DNA sequences into the cellr genome. J. Virol. 71: 3299–3306.

Kotin, R M, et al, 1990, PNAS USA, 87:2211–2215.

Samulski. R J et al, 1991, EMBO J. 10:3941–3950.

Carter, B J. in "Handbook of Parvoviruses", ed. P. Tijsser, CRC Press, pp. 155–168, Samulski, R W096/36364.

Horer, M., Weger, S., Butz, K., Hoppe-Seyler, F., Geisen, C., Kleinschmidt, J. (1995) Mutational analysis of adeno-associated virus Rep protein-mediated inhibition of heterologous and homologous promoters. J. Virol. 69: 5485–5496.

D. S. Im and N. Muzyczka Cell 1990, 61, 447–457.

Parks, R. J., L. Chen, M. Anton, U. Sankar, M. A. Rudnicki, and F. L. Graham (1996). A "helper" dependent adenovirus vector system: removal of virus by cre-mediated excision of the viral packaging signal. Proc. Natl. Acad. Sci. USA 93:13656–13570.

Sambrook J., AND.F. Fritsch and T. Maniatis, "Molecular Cloning: A Laboratory Manual", 2nd ed. Cold Spring Harbor Laboratory, Cold Spring Harbor, N.Y. 1989.

Samulski, R. J., Chang L.-S. and T. Shenk (1987) A recombinant plasmid from which an infectious adeno-associated virus genome can be excised in vitro and its use to study viral replication. J. Virol 61: 3096–3101.

Shelling, A. N., and M. G. Smith. (1994). Targeted integration of transfected and infected adeno-associated virus vectors containing the neomycin resistance gene. Gene Ther. 1:165–169.

Surosky, R. T., M. Urabe, S. G. Godwin, S. A. McQuiston, G. J. Kurtzman, K. Ozawa, and G. Natsoulis (1997). Adeno-associated virus Rep proteins target DNA sequences to a unique site in the human genome. J. virol. 71: 7951–7959.

Yang, Q., Chen, F. and J. P. Trempe (1994). Characterisation of cell lines that inducibly express the adeno-associated virus Rep proteins. J. Virol. 68: 4847–4856.

What is claimed is:

1. An isolated nucleic acid molecule encoding a Rep 68 or Rep 78 mutein of an Adeno-associated virus comprising a first nucleotide sequence ligated in frame to a second nucleotide sequence, wherein said first nucleotide sequence encodes a Rep 68 or Rep 78 protein containing a mutation within the region from amino acid residue 480 to amino acid residue 520 of the protein such that nuclear localization of Rep 68 or Rep 78 is totally inactivated while maintaining normal function, and said second nucleotide sequence encodes a hormone binding domain of a steroid hormone receptor that includes a nuclear localization signal.

2. An expression vector for expressing a Rep 68 or Rep 78 mutein in a recombinant cell wherein said expression vector comprises a nucleic acid molecule of claim 1.

3. A host cell which expresses a Rep 68 or Rep 78 mutein wherein said host cell contains the expression vector of claim 2.

4. A process of expressing a Rep 68 or Rep 78 mutein in a recombinant host cell, comprising:

(a) transfecting the expression vector of claim 2 into a suitable host cell; and, (b) culturing the host cells of step (a) under conditions which allow expression of said mutein from said expression vector.

5. An isolated nucleic acid molecule of claim 1, wherein said second nucleotide sequence is located 3' to said first nucleotide sequence.

6. An isolated nucleic acid molecule of claim 1, wherein said second nucleotide sequence is located 5' to said first nucleotide sequence.

7. An isolated nucleic acid molecule of claim 1, wherein said second nucleotide sequence is located within the portion of said first nucleotide sequence encoding from amino acid residue 480 to the carboxy-terminus of the Rep 68 or Rep 78 protein.

8. An isolated nucleic acid molecule of claim 1, wherein said first nucleotide sequence encodes a Rep 68 or Rep 78 protein containing a deletion from amino acid residue 485 to amino acid residue 520.

9. An isolated nucleic acid molecule of claim 1, wherein said first nucleotide sequence encodes a Rep 68 or Rep 78 protein containing a deletion from amino acid residue 485 to the carboxy-terminus of the protein.

10. An isolated nucleic acid molecule of claim 1, wherein said second nucleotide sequence encodes the hormone binding domain of a mammalian steroid hormone receptor.

11. An isolated nucleic acid molecule of claim 1, wherein said second nucleotide sequence encodes the hormone binding domain of a human steroid hormone receptor.

12. An isolated nucleic acid molecule of claim 1, wherein said second nucleotide sequence encodes the hormone binding domain of human progesterone receptor.

13. An isolated nucleic acid molecule of claim 12, wherein said second nucleotide sequence encodes from about amino acid residue 640 to about amino acid residue 933 of the human progesterone receptor.

14. An isolated nucleic acid molecule of claim 12, wherein said second nucleotide sequence encodes from amino acid residue 640 to amino acid residue 891 of the human progesterone receptor.

15. An isolated nucleic acid molecule of claim 9, wherein said second nucleotide sequence encodes from amino acid residue 635 to amino acid residue 891 of the human progesterone receptor.

* * * * *

SEQUENCE LISTING

<160> NUMBER OF SEQ ID NOS: 18

<210> SEQ ID NO 1
<211> LENGTH: 28
<212> TYPE: DNA
<213> ORGANISM: Artificial Sequence
<220> FEATURE:
<223> OTHER INFORMATION: oligonucleotide synthesizer

<400> SEQUENCE: 1
catcagatct atgccggggt tttacgag                                28

<210> SEQ ID NO 2
<211> LENGTH: 28
<212> TYPE: DNA
<213> ORGANISM: Artificial Sequence
<220> FEATURE:
<223> OTHER INFORMATION: oligonucleotide synthesizer

<400> SEQUENCE: 2
catcagatct tcagagagag tgtcctcg                                28

<210> SEQ ID NO 3
<211> LENGTH: 23
<212> TYPE: DNA
<213> ORGANISM: Artificial Sequence
<220> FEATURE:
<223> OTHER INFORMATION: oligonucleotide synthesizer

<400> SEQUENCE: 3
tggtcgggtg gctcgtggac aag                                    23

<210> SEQ ID NO 4
<211> LENGTH: 40
<212> TYPE: DNA
<213> ORGANISM: Artificial Sequence
<220> FEATURE:
<223> OTHER INFORMATION: oligonucleotide synthesizer

<400> SEQUENCE: 4
ctctcctcta gatcagaatt catgctccac ctcaaccacg                   40

<210> SEQ ID NO 5
<211> LENGTH: 42
<212> TYPE: DNA
<213> ORGANISM: Artificial Sequence
<220> FEATURE:
<223> OTHER INFORMATION: oligonucleotide synthesizer

<400> SEQUENCE: 5
ctctcctcta gatcaggctc caccttttt gacgtagaat tc                 42

<210> SEQ ID NO 6
<211> LENGTH: 40
<212> TYPE: DNA
<213> ORGANISM: Artificial Sequence
<220> FEATURE:
<223> OTHER INFORMATION: oligonucleotide synthesizer

<400> SEQUENCE: 6
ctcctctcta gatcactcac ttatatctgc gtcactgggg                   40

<210> SEQ ID NO 7
<211> LENGTH: 42

```
<212> TYPE: DNA
<213> ORGANISM: Artificial Sequence
<220> FEATURE:
<223> OTHER INFORMATION: oligonucleotide synthesizer

<400> SEQUENCE: 7
ctcctctcta gatcacgcgt ctgacgtcga tggctgcgca ac                    42

<210> SEQ ID NO 8
<211> LENGTH: 20
<212> TYPE: DNA
<213> ORGANISM: Artificial Sequence
<220> FEATURE:
<223> OTHER INFORMATION: oligonucleotide synthesizer

<400> SEQUENCE: 8
gtagcatggc gggttaatca                                             20

<210> SEQ ID NO 9
<211> LENGTH: 21
<212> TYPE: DNA
<213> ORGANISM: Artificial Sequence
<220> FEATURE:
<223> OTHER INFORMATION: oligonucleotide synthesizer

<400> SEQUENCE: 9
gcgcgcagaa gccagtagag c                                           21

<210> SEQ ID NO 10
<211> LENGTH: 27
<212> TYPE: DNA
<213> ORGANISM: Artificial Sequence
<220> FEATURE:
<223> OTHER INFORMATION: oligonucleotide synthesizer

<400> SEQUENCE: 10
ttaactacaa ggaacccta gtgatgg                                      27

<210> SEQ ID NO 11
<211> LENGTH: 27
<212> TYPE: DNA
<213> ORGANISM: Artificial Sequence
<220> FEATURE:
<223> OTHER INFORMATION: oligonucleotide synthesizer

<400> SEQUENCE: 11
ttaactacaa ggaacccta gtgatgg                                      27

<210> SEQ ID NO 12
<211> LENGTH: 16
<212> TYPE: PRT
<213> ORGANISM: Artificial Sequence
<220> FEATURE:
<223> OTHER INFORMATION: adeno-associated virus

<400> SEQUENCE: 12

Pro Lys Arg Val Arg Glu Ser Val Ala Gln Pro Ser Thr Ser Ser Asp
1               5                   10                  15

<210> SEQ ID NO 13
<211> LENGTH: 13
<212> TYPE: PRT
<213> ORGANISM: Artificial Sequence
<220> FEATURE:
<223> OTHER INFORMATION: adeno-associated virus

<400> SEQUENCE: 13
```

```
Lys Lys Arg Pro Ala Pro Ser Asp Ala Asp Ile Ser Glu
1               5                   10
```

<210> SEQ ID NO 14
<211> LENGTH: 7
<212> TYPE: PRT
<213> ORGANISM: Artificial Sequence
<220> FEATURE:
<223> OTHER INFORMATION: adeno-associated virus

<400> SEQUENCE: 14

```
Tyr Tyr Lys Lys Gly Gly Ala
1               5
```

<210> SEQ ID NO 15
<211> LENGTH: 17
<212> TYPE: PRT
<213> ORGANISM: Artificial Sequence
<220> FEATURE:
<223> OTHER INFORMATION: synthetic

<400> SEQUENCE: 15

```
Val Glu His Glu Phe Gly Gly Arg Lys Phe Lys Lys Phe Asn Lys Val
1               5                   10                  15

Arg
```

<210> SEQ ID NO 16
<211> LENGTH: 22
<212> TYPE: PRT
<213> ORGANISM: Artificial Sequence
<220> FEATURE:
<223> OTHER INFORMATION: synthetic

<400> SEQUENCE: 16

```
Val Glu His Glu Phe Tyr Val Lys Lys Gly Gly Ala Leu Glu Phe Lys
1               5                   10                  15

Lys Phe Asn Lys Val Arg
            20
```

<210> SEQ ID NO 17
<211> LENGTH: 19
<212> TYPE: PRT
<213> ORGANISM: Artificial Sequence
<220> FEATURE:
<223> OTHER INFORMATION: synthetic

<400> SEQUENCE: 17

```
Val Glu His Glu Phe Tyr Val Lys Lys Gly Gly Ala Leu Glu Phe Asn
1               5                   10                  15

Lys Val Arg
```

<210> SEQ ID NO 18
<211> LENGTH: 10
<212> TYPE: PRT
<213> ORGANISM: Artificial Sequence
<220> FEATURE:
<223> OTHER INFORMATION: synthetic

<400> SEQUENCE: 18

```
Ala Asp Arg Leu Ala Arg Gly His Ser Leu
1               5                   10
```